United States Patent [19]
Young et al.

[11] Patent Number: 5,114,715
[45] Date of Patent: May 19, 1992

[54] METHODS OF USE AND COMPOSITIONS OF (S)-ISOFLURANE AND (S)-DESFLURANE

[75] Inventors: James W. Young, Still River; Steven Brandt, Marlborough, both of Mass.

[73] Assignee: Sepracor Inc., Marlborough, Mass.

[21] Appl. No.: 619,780

[22] Filed: Nov. 29, 1990

[51] Int. Cl.$^5$ .................. C07C 41/44; C07C 43/192
[52] U.S. Cl. .................. 424/400; 424/435; 514/816; 568/684
[58] Field of Search .......... 424/400, 435; 514/816; 568/684

[56] References Cited

U.S. PATENT DOCUMENTS

| | | | |
|---|---|---|---|
| 3,469,011 | 10/1970 | Terrell | 514/722 |
| 3,535,388 | 10/1970 | Terrell | 568/684 |
| 3,897,502 | 7/1975 | Russell et al. | 568/683 |
| 3,970,710 | 7/1976 | Wolownik | 568/842 |
| 3,980,714 | 9/1976 | Siegemund et al. | 514/816 |
| 3,981,927 | 9/1976 | Siegemund et al. | 514/816 |
| 4,220,664 | 9/1980 | McCarty et al. | 568/684 |
| 4,262,144 | 4/1981 | McCarty et al. | 568/684 |
| 4,273,947 | 6/1981 | Novotny | 568/842 |
| 4,584,303 | 4/1986 | Huang et al. | 514/326 |
| 4,590,310 | 5/1986 | Townsend et al. | 568/842 |
| 4,762,856 | 8/1988 | Terrell | 514/722 |
| 4,855,511 | 8/1989 | Halpern et al. | 568/683 |

OTHER PUBLICATIONS

Kendig et al., *Anesthesiology*, 39(5): 518-524 (1973).
Meinwald et al., *Science*, 251: 560-561 (1991).
Brown et al., *British Journal of Anaesthesia*, 59: 14-23 (1987).
Clark et al., *Anesthesiology*, 39(3): 261-270 (1973).
Eger, *British Journal of Anaesthesia* 56: 71S-99S (1984).
Jones et al., *British Journal of Anaesthesia*, 65: 11-15 (1990).
Jones et al., *Anesthesie et Analgesie*, 70: 3-7 (1990).
Christys et al., *British Journal of Anaesthesia*, 62: 624-627 (1989).
Yasuda et al., *Anesthesie et Analgesie*, 71: 240-248 (1990).
Koblin et al., *Anesthesie et Analgesie*, 60: 464-470 (1981).
Hymes, *Anesthesie et Analgesie*, 64: 367-368 (1985).
McGuire et al., *Anaesthesia*, 45: 124-127 (1990).
Holmes et al., *Anesthesie et Analgesie*, 71: 249-253 (1990).
Knight et al., *Antimicrobial Agents and Chemotherapy*, 20(3): 298-306 (1981).
Koblin et al., *Anesthesiology*, 54: 314-317 (1981).
Freye et al., *Anaesthesist*, 34: 670-674 (1985).
Terrell, et al., *Journal of Medicinal Chemistry*, 14(6): 517-519.

*Primary Examiner*—Thurman K. Page
*Assistant Examiner*—Carlos Azpuru
*Attorney, Agent, or Firm*—Pennie & Edmonds

[57] ABSTRACT

Disclosed is a method of inducing and maintaining anesthesia while avoiding concomitant liability of adverse effects comprising administering by inhalation to a warm blooded animal in need of anesthesia an amount sufficient to induce and maintain anesthesia but insufficient to cause said adverse effects, of (S)-isoflurane or (S)-desflurane, substantially free of its (R)-stereoisomer. Also disclosed are novel compositions of these compounds for use in the above disclosed method.

10 Claims, No Drawings

METHODS OF USE AND COMPOSITIONS OF (S)-ISOFLURANE AND (S)-DESFLURANE

TABLE OF CONTENTS

1. Background of the Invention
2. Summary of the Invention
3. Detailed Description of the Invention

1. BACKGROUND OF THE INVENTION

This invention relates to a novel method of inducing and maintaining anesthesia while diminishing concomitant liability of adverse effects by the administration of (S)-isoflurane or (S)-desflurane and novel compositions of these compounds for use in the above disclosed novel method.

The active compounds of the method and composition of the present invention are optical isomers of the compounds isoflurane and desflurane.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (−) and d and l are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of propranolol, which is known to be 100 times more potent than the D-enantiomer.

Furthermore, optical purity is important since certain isomers may actually be deleterious rather than simply inert. For example, the D-enantiomer of thalidomide was a safe and effective sedative when prescribed for the control of morning sickness during pregnancy. However, its L-thalidomide counterpart was discovered to be a potent teratogen.

Isoflurane is 1-chloro-2,2,2-trifluoroethyl difluoromethyl ether. It has the structural formula:

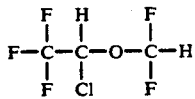

Desflurane is 2-(difluoromethoxy)-1,1,1,2-tetrafluoroethane. It has the structural formula:

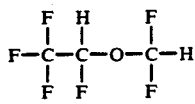

The racemic mixture forms of isoflurane and desflurane are general anesthetic drugs used to induce and maintain anesthesia. The state of anesthesia is a drug induced absence of perception of all sensations. General anesthesia is used most often during surgical procedures. Isoflurane, and desflurane are non-flammable liquids, administered by inhalation. This route of administration makes the effective dose and time course of action more predictable and more easily controlled.

Isoflurane has certain advantages over other general anesthetics such as halothane or ethrane. Its potency is between that of halothane and enflurane. Induction and recovery from anesthesia is more rapid with isoflurane than with halothane or ethrane however it is still slow. In addition, isoflurane is slightly less depressant to respiration and the cardiovascular system in the dog than either halothane or ethrane, however it still causes respiratory depression. Isoflurane shows significantly less sensitization of the heart to epinephrine induced arrhythmias than halothane. All commonly used muscle relaxants are markedly potentiated with isoflurane, the effect being most profound with the nondepolarizing type.

Desflurane, which is currently in clinical trials, also has certain clinical advantages over other anesthetic agents such as isoflurane. Scrips, 1481, pg. 27, (1990).

While isoflurane and desflurane have certain advantages over other anesthetic agents, they also have disadvantages which are primarily adverse effects which are in general dose dependent extensions of pharmaco-physiologic effects of the compounds. These adverse effects include respiratory depression, hypotension, arrhythmias, shivering, nausea, vomiting, ileus, malignant hyperthermia, elevated white blood count and slow recovery from anesthesia. These adverse effects are primarily due to the high dose of the racemic mixture of isoflurane and desflurane needed to induce and maintain anesthesia.

It is therefore desirable to find a compound with the advantages of isoflurane and desflurane which would not have the above described disadvantages.

2. SUMMARY OF THE INVENTION

It has now been discovered that the (S)-stereoisomer of isoflurane or the (S)-stereoisomer of desflurane can be administered by inhalation to a warm-blooded animal in low concentrations wherein anesthesia can be induced and maintained, and the adverse effects associated with the administration of the racemic mixture of isoflurane or desflurane are diminished.

3. DETAILED DESCRIPTION OF THE INVENTION

The present invention encompasses a method of inducing and maintaining anesthesia while diminishing concomitant liability of adverse effects comprising administering by inhalation to a warm blooded animal in need of anesthesia an amount sufficient to induce and maintain anesthesia but insufficient to cause said adverse effects, of (S)-isoflurane, or (S)-desflurane substantially free of their (R)-stereoisomer.

Such method of administration may also include coadministration of oxygen or oxygen containing gas mixtures in amounts sufficient to sustain life.

Also embodied in the present invention is an anesthetic composition adapted for inducing and maintaining anesthesia in a warm-blooded animal comprising an amount sufficient to induce and maintain anesthesia but insufficient to cause adverse effects, of (S)-isoflurane or (S)-desflurane, which are substantially free of its (R)-stereoisomer.

The racemic mixture of isoflurane or desflurane, (i.e., a mixture of R and S stereoisomers) are effective agents for inducing and maintaining anesthesia, however the racemic mixture causes adverse effects. The use of the (S)-isomer of isoflurane or the (S)-isomer of desflurane, diminishes these adverse effects by allowing the anesthetic drug to be given in a lower dose or lower concentration. Thus, it is more desirable to use the (S)-isomer of isoflurane or the (S)-isomer of desflurane to induce and maintain anesthesia.

The term "adverse effects" includes but is not limited to respiratory depression, hypotension, arrhythmias, shivering, nausea, vomiting, ileus, malignant hyperthermia, elevated white blood count and slow recovery from anesthesia.

The term "substantially free of its (R)-stereoisomer" as used herein means that the composition contains at least 90% by weight of (S)-isoflurane or (S)-desflurane and 10% by weight or less of (R)-isoflurane or (R)-desflurane. In the most preferred embodiment the term "substantially free of its (R)-stereoisomer" means that the composition contains at least 95% by weight (S)-isoflurane or (S)-desflurane and 5% or less of (R)-isoflurane or (R)-desflurane.

Isoflurane and its preparation are disclosed in U.S. Pat. No. 3,535,388 incorporated herein by reference. Isoflurane is a clear colorless stable liquid containing no additives or chemical stabilizers. It has a mildly pungent, musty, ethereal odor. Isoflurane has the following physical properties: Boiling point 48.5° C., molecular weight 184.5, vapor pressure 238 mm Hg at 20° C., and specific gravity 1.496.

Desflurane as a racemic mixture can be prepared by the method described in U.S. Pat. No. 3,987,502 which is incorporated by reference. Desflurane is normally a clear, colorless liquid with a slight non-pungent odor. It has the following physical properties: boiling point 23.5° C., molecular weight 168, vapor pressure (est.) 660 mm Hg at 20° C., and specific gravity 1.44. The compound is non-flammable, and soda lime stable.

The general reaction scheme and method for producing optically pure isoflurane or desflurane is as follows:

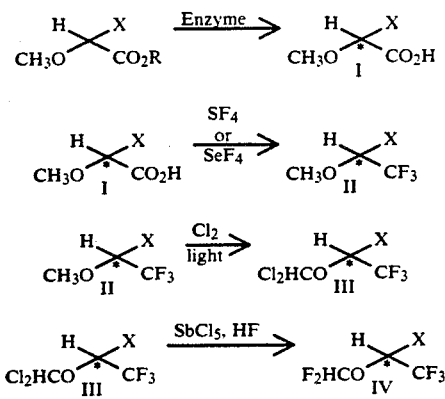

wherein:
X = Cl (isoflurane)
X = F (desflurane)
R =
—alkyl
—alkoxyalkyl (—CH$_2$(CH$_2$)$_n$OCH$_3$)
—CH$_2$CN —(CH$_2$)$_n$SO$_3$—
—(CH$_2$)$_n$OSO$_3$—
—(CH$_2$)$_n$N$^+$(CH$_3$)$_3$—
and
n is 0,1,2, or 3.

The above reaction for producing optically pure isoflurane or desflurane involves using esters of racemic 2-methoxy-2-haloacetic acid as a starting material.

Central to the reaction is the production of the key optically pure 2-methoxy-2-haloacetic acid (I). This is accomplished through the kinetic enzymatic resolution of the starting racemic 2-methoxy-2-haloacetic acid ester to give the desired optically pure 2-methoxy-2-halo compound as the free acid. Conversion of this compound to the corresponding trifluoromethyl compound is then accomplished through any one of a number of standard means, including treatment with sulfur tetrafluoride or selenium tetrafluoride. Organic Reactions, 21 64 (1984). The 2-halo-2-methoxy-1,1,1-trifluoroethane produced can then be converted by the synthesis disclosed in, J. Med. Chem. 14, 517 (1971); and U.S. Pat. No. 3,469,011 (1966). This reaction involves free radical halogenation of the methoxy group to yield the dichloro derivative, followed by exchange of chloride for fluoride using antimony pentafluoride in hydrofluoric acid.

The enzymes used in the above synthesis include, but are not limited to, serine, thiol and carboxy-acid proteases, neutral microbial metalloproteases, other microbial proteases and mammalian peptidases. Specific examples from another class of enzymes include, but are not limited to, fatty acid esterases (E.C. 3.1.1.1), arylester hydrolases (E.C. 3.1.1.2), triacylglycerol acylhydrolases (E.C. 3.1.1.3.), and other enzymes that are known to cleave ester and amide linkages. The term E.C. followed by a series of numbers as used herein, provides the identification of an enzyme pursuant to the Recommendations of the Commission on Biochemical Nomenclature, Elsevier, Amsterdam, The Nomenclature and Classifictaion of Enzymes (1972) P. 17–22.

For example, generally preferred proteases include, but are not limited to, the alkaline proteases from *Aspergillus* sp. and *Bacillus* sp.; preferred esterases include, but are not limited to, procine liver esterase (E.C. 3.1.1.1); and preferred lipases include, but are not limited to, the lipase from *Candida cylindracea* (also known as *C. rugosa*) (E.C. 3.1.1.3). These are preferred because of their availability, high stereospecificity and broad substrate range.

Other proteases include, but are not limited to: serine proteases from animal sources, such as α-chymotrypsin E.C. 3.4.21.1) and Trypsin (E.C. 3.4.21.4), both isolated from bovine and swine pancreas; serine proteases from plant sources; carboxy-acid proteases from animal sources, such as Pepsin (E.C. 3.4.23.1), Chymosin (E.C. 3.4.23.4), and Carboxypeptidase A (E.C. 3.4.17.1); serine proteases from microorganisms, generally referred to as subtilisins (E.C. 3.4.21.14) but isolated from a variety of microorganisms, including naturally occurring specie and genetically manipulated specie, of such microorganisms as *Bacillus subtilis amylolicuefaciens*, *Bacillus amylosaccharicus* and *Bacillus licheniformis*; serine proteases from *Aspergillus* sp., such as *Aspergillus oryzae* and *Aspergillus flavus*, which may be classified as subtilisins but may also be called Aspergillus alkaline proteases; microbial metallo-neutral proteases (E.C. 3.4.24.4) isolated from a variety of sources such as *Asperoillus oryzae*, *Bacillus* sp. and *Streptomyces griseus*;

and other microbial proteases (E.C. 3.4.23.6) isolated from sources such as the genera *Aspergillus, Bacillus, Mucor, Penicillium, Pseudomonas, Rhizoous, Serratia, Staphylococcus, Streptococcus, Streotomyces* and *Tritirachium*. Proteases isolated from mammalian blood, pancreas, spleen, submaxillary glands and gastro-intestinal mucosa may also be used.

Other lipases include, but are not limited to, those isolated from micro-organisms, such as *Pseudomonas aeruginosa, Pseudomonas fluorecens, Rhizopus arrhizus, Rhizopus delemar, Rhizopus niveus, Rhizopous oryzae, Rhizopus japonicus, Chromobacterium viscosum, Geotrichium candidum, Asperfillus niger, Aspergillus, sojae, Aspergillus oryzae, Mucor miehei, Achromobacter lipolyticum, Alcaligenes* sp., *Arthrobacter* sp. and *Candida lipolytica*. Pancreatic lipases from various mammalian species and lipase derived from wheat germ may also be employed. Other esterases derived from mammalian sources include, but are not limited to, carboxyl esterase (E.C. 3.1.1.1.), carboxypeptidase A (E.C. 3.4.17.1), acetyl cholinesterase (E.C. 3.1.1.7), pepsin (E.C. 3.4.23.1) and trypsin (E.C. 3.4.21.4). Other microbial sources include *Bacillus thermoproteolyticus* (for thermolysin), *Bacillus amyloliquefaciens* and *Streptomyces griseus* as well as papain (E.C. 3.4.22.2) derived from *Papaya sp.*

Depending upon the source, lipases and esterases have a working pH range from about 2 to 10, with their optimum pH generally falling between 5.0 and 8.5. The temperature range for most enzymes takes place from about 15 to 70° C., with the enzymes usually performing most effectively in the range from about 20-45° C.

In addition to isolated and purified enzymes, it should be noted that the processes used may also be carried out employing relatively impure and/or heterogeneous enzyme preparations, such as those derived from cell extracts, cell lysates, partially purified enzyme isolates and whole cells, albeit at some reduction in the enzymatic activity. Enzyme can also be immobilized on solid, non-membrane supports by conventional means; such as, covalent binding, absorption, matrix entrapment, ion-exchange, or microencapsulation. Indeed, enzymes contained within whole cells, whether viable or not, may also be used in the practice of this invention, and accordingly it is intended that the term "enzyme" as used herein is meant to broadly include biocatalytic enzymes in all of these forms.

The (S)-isomers of isoflurane or desflurane lend themselves to effective use an inhalant anesthetics by themselves or in respirable mixtures containing life-supporting concentrations of oxygen, with or without other inhalation anesthetics, such as nitrous oxide. Administration of the compound may be by any of the well known techniques for administering general inhalation anesthetics, for example by using the open drop or semiclosed systems.

The effective amount of (S)-isoflurane or (S)-desflurane to be employed in the method of the present invention depends on the level of anesthesia to which the mammal is to be brought, the rate at which anesthesia is to be induced and the length of time over which anesthesia is to be maintained. Minor volume percentages of the compound in oxygen can often be employed. The lower amount of the (S)-isomer of isoflurane or the (S)-isomer of desflurane used in the method and composition of the present invention is sufficient to provide a significant anesthetic effect but not so much as to produce unacceptable adverse effects. The amount of anesthesia to be used can be regulated, starting with a small amount of the compound and gradually increasing the amount until the desired plane of anesthesia is reached. By then monitoring the physical reactions of the mammal, as is the usual procedure, the duration and plane of anesthesia can be readily controlled.

If a vaporizer is used to deliver (S)-isoflurane or (S)-desflurane the concentration being delivered should be known. The delivered concentration from such a vaporizer may be calculated using the formula:

$$\% \text{ (S)-isoflurane or desflurane} = \frac{100 \, P_V F_V}{F_T(P_A - P_V)}$$

wherein:
$P_A$ = Pressure of atmosphere
$P_V$ = Vapor pressure of isoflurane
$F_V$ = Flow of gas through vaporizer (ml/min)
$F_T$ = Total gas flow (ml/min)

The usual concentration of (S)-isoflurane or (S)-desflurane to induce anesthesia is 0.5 to 5.0%.

The usual concentration of (S)-isoflurane or (S)-desflurane administered to maintain anesthesia while oxygen is administered concomitantly is 0.5 to 3.5%.

The usual concentration of (S)-isoflurane or (S)-desflurane administered to maintain anesthesia while nitrous oxide is administered concomitantly is 0.5 to 2.5%.

What is claimed is:

1. A method of inducing and maintaining anesthesia while diminishing the concomitant liability of adverse effects associated with the administration of racemic isoflurane or desflurane, comprising administering by inhalation to a warm blooded animal including a mammal in need of anesthesia an amount sufficient to induce and maintain anesthesia but insufficient to cause adverse effects, of (S)-isoflurane or (S)-desflurane, wherein when (S)-isoflurane is administered said amount contains about 90% or more by weight of (S)-isoflurane and about 10% or less by weight of (R)-isoflurane, or when (S)-desflurane is administered said amount contains about 90% or more by weight of (S)-desflurane and about 10% or less by weight of (R)-desflurane.

2. The method of claim 1 wherein (S)-isoflurane or (S)-desflurane is administered to induce anesthesia in an inspired concentration of about 0.5 to about 5.0%.

3. The method of claim 1 wherein (S)-isoflurane or (S)-desflurane is administered to maintain anesthesia in an inspired concentration of about 0.5 to about 2.5% while nitrous oxide is administered concomitantly.

4. The method of claim 1 wherein (S)-isoflurane or (S)-desflurane is administered to maintain anesthesia in an inspired concentration of about 0.5 to about 3.5% while oxygen is administered concomitantly.

5. The method of claim 2 wherein said amount of (S)-isoflurane or (S)-desflurane is greater than approximately 95% of weight of the total compound used.

6. The method of claim 2 wherein said adverse effects are selected from the group consisting of respiratory depression, hypotension, arrhythmias, shivering, nausea, vomiting, ileus, malignant hyperthermia, elevated white blood count, and slow recovery from anesthesia.

7. An anesthetic composition adapted for inducing and maintaining anesthesia in a warm-blooded animal comprising an amount, sufficient to induce and maintain anesthesia but insufficient to cause adverse effects associated with the administration of racemic isoflurane or desflurane, of (S)-isoflurane or (S)-desflurane, wherein when (S)-isoflurane is administered said amount contains about 90% or more by weight of (S)-isoflurane and about 10% or less by weight of (R)-isoflurane or when (S)-desflurane is administered said amount contains about 90% or more by weight of (S)-desflurane and about 10% or less by weight of (R)-desflurane for anesthesia in an inspired concentration of about 0.5% to about 5.0%.

8. A composition according to claim 7 which contains (S)-isoflurane or (S)-desflurane.

9. A composition according to claim 7 adapted for inhalation administration.

10. A composition according to claim 7 wherein (S)-inoflurane or (S)-desflurane is administered together with a pharmaceutically acceptable carrier.

* * * * *